(12) United States Patent
Slater (10) Patent No.: US 11,662,338 B2
(45) Date of Patent: May 30, 2023

(54) SYSTEM AND METHOD FOR MEASURING SAG IN A FLUID (71) Applicant: SCHLUMBERGER TECHNOLOGY CORPORATION, Sugar Land, TX (US)

(72) Inventor: Kenneth Slater, Sealy, TX (US)

(73) Assignee: SCHLUMBERGER TECHNOLOGY CORPORATION, Sugar Land, TX (US)

( * ) Notice: Subject to any disclaimer, the term of this patent is extended or adjusted under 35 U.S.C. 154(b) by 217 days.

(21) Appl. No.: 17/114,544

(22) Filed: Dec. 8, 2020

(65) Prior Publication Data
US 2022/0178905 A1 Jun. 9, 2022

(51) Int. Cl.
*G01N 33/28* (2006.01)
*G01N 9/00* (2006.01)
*G01N 24/08* (2006.01)

(52) U.S. Cl.
CPC .......... *G01N 33/2823* (2013.01); *G01N 9/00* (2013.01); *G01N 24/08* (2013.01)

(58) Field of Classification Search
CPC ........ G01N 9/36; G01N 33/2823; G01N 9/00; G01N 24/08
See application file for complete search history.

(56) References Cited

U.S. PATENT DOCUMENTS

| | | | | |
|---|---|---|---|---|
| 4,805,443 A | * | 2/1989 | Schroeder | G01N 15/0806 220/303 |
| 5,086,646 A | * | 2/1992 | Jamison | G01N 9/00 73/61.63 |
| 7,845,212 B1 | | 12/2010 | Bi | |
| 10,145,775 B2 | * | 12/2018 | Savari | G01N 7/00 |
| 10,520,484 B2 | * | 12/2019 | Miller | G01N 33/2823 |
| 2010/0133204 A1 | | 6/2010 | Tehrani et al. | |
| 2015/0135815 A1 | | 5/2015 | Blue et al. | |
| 2018/0172660 A1 | | 6/2018 | Miller et al. | |
| 2022/0178906 A1 | | 6/2022 | Slater et al. | |

FOREIGN PATENT DOCUMENTS

EP 0417885 A2 3/1991

OTHER PUBLICATIONS

International Search Report and Written Opinion issued in International Patent application PCT/US2021/072782 dated Mar. 31, 2022, 11 pages.

* cited by examiner

Primary Examiner — John Fitzgerald
Assistant Examiner — Jean F Morello (57) ABSTRACT

A device for aging a drilling fluid includes a housing. The device also includes a lower cap that is configured to be coupled to or integral with a lower end of the housing. The device also includes an upper cap that is configured to be coupled to an upper end of the housing. The upper cap has an upper cap hole formed therethrough. The device also includes a piston that is configured to be positioned within the housing and between the lower and upper caps. The piston is configured to move axially within the housing in response to a pressure differential across the piston. The piston has a first piston hole formed therethrough.

17 Claims, 10 Drawing Sheets

SYSTEM AND METHOD FOR MEASURING SAG IN A FLUID

BACKGROUND

A drilling fluid (also referred to as drilling mud) is a fluid, or a mixture of a fluid and solid particles, that is used to drill a wellbore in a subterranean formation. Drilling fluids may be water, oil, or synthetic-based. Oil or synthetic-based fluids are oftentimes oil continuous-phase emulsions, although some water-continuous phase emulsion fluids exist. The density of the drilling fluid may be modified to facilitate drilling operations. For example, a weighting agent, such as barium sulfate (i.e., barite), in the form of a fine solid, may be added to the drilling fluid to increase the density of the drilling fluid to maintain primary well control, aid in wellbore integrity, and help prevent subterranean formation influxes from entering the wellbore, as well as other operational reasons. If the drilling fluid is static, or is flowing at low rates, the drilling fluid may experience sag (also referred to as barite sag). Barite sag occurs when the weighting material (e.g., barite) is no longer homogenously dispersed in the drilling fluid due to stratification or settlement. Barite sag can occur in dynamic or static conditions and leads to drilling fluid density fluctuations in the wellbore.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

A device for aging a drilling fluid is disclosed. The device includes a housing. The device also includes a lower cap that is configured to be coupled to or integral with a lower end of the housing. The device also includes an upper cap that is configured to be coupled to an upper end of the housing. The upper cap has an upper cap hole formed therethrough. The device also includes a piston that is configured to be positioned within the housing and between the lower and upper caps. The piston is configured to move axially within the housing in response to a pressure differential across the piston. The piston has a first piston hole formed therethrough.

A system is also disclosed. The system may be used for determining a sag profile of a drilling fluid that has been exposed to elevated temperature and pressure conditions. The system includes a device. The device includes a housing that is substantially cylindrical and defines an inner volume. The inner volume is configured to receive the drilling fluid. The device also includes a lower cap that is coupled to a lower end of the housing. The lower cap includes a base and a wall extending upwardly from the base. The wall is configured to be positioned at least partially within the housing such that an inner volume of the lower cap at least partially overlaps with the inner volume of the housing. The wall includes threads on an outer surface thereof that are configured to engage with corresponding threads on an inner surface of the housing. The device also includes an upper cap coupled to an upper end of the housing. The upper cap has an upper cap hole formed therethrough to allow a hydraulic fluid to flow therethrough into the inner volume of the housing. The device also includes a piston positioned within the housing and between the lower and upper caps. The piston is configured to move axially within the housing in response to a pressure differential between the drilling fluid and the hydraulic fluid across the piston. The piston has a first piston hole and a second piston hole formed therethrough. The device also includes a plug configured to be positioned at least partially within the first piston hole. The device also includes a rupture disk configured to be positioned at least partially within the second piston hole. The system also includes a vessel defining an inner volume, wherein the device is configured to be introduced into the inner volume of the vessel. A temperature and a pressure of the drilling fluid in the device are configured to be increased while the device is positioned within the vessel.

A method for determining a sag profile of a first fluid that has been exposed to elevated temperature and pressure conditions is also disclosed. The method includes introducing the first fluid into a housing of a device. The method also includes introducing a piston into the housing. The piston is at least partially above the first fluid. The method also includes coupling an upper cap to an upper end of the housing. The method also includes inserting the device into a vessel. The method also includes heating the first fluid to a predetermined temperature within the vessel. The method also includes pressurizing the first fluid to a predetermined pressure within the vessel.

BRIEF DESCRIPTION OF THE DRAWINGS

The present disclosure is best understood from the following detailed description when read with the accompanying Figures. It is emphasized that, in accordance with the standard practice in the industry, various features are not drawn to scale. In fact, the dimensions of the various features may be arbitrarily increased or reduced for clarity of discussion.

DETAILED DESCRIPTION

Illustrative examples of the subject matter claimed below will now be disclosed. In the interest of clarity, not all features of an actual implementation are described in this specification. It will be appreciated that in the development of any such actual implementation, numerous implementation-specific decisions may be made to achieve the developers' specific goals, such as compliance with system-related and business-related constraints, which will vary from one implementation to another. Moreover, it will be appreciated that such a development effort, even if complex and time-consuming, would be a routine undertaking for those of ordinary skill in the art having the benefit of this disclosure.

Further, as used herein, the article "a" is intended to have its ordinary meaning in the patent arts, namely "one or more." Herein, the term "about" when applied to a value generally means within the tolerance range of the equipment used to produce the value, or in some examples, means plus or minus 10%, or plus or minus 5%, or plus or minus 1%, unless otherwise expressly specified. Further, herein the term "substantially" as used herein means a majority, or almost all, or all, or an amount with a range of about 51% to about 100%, for example. Moreover, examples herein are intended to be illustrative only and are presented for discussion purposes and not by way of limitation.

Figure 1:
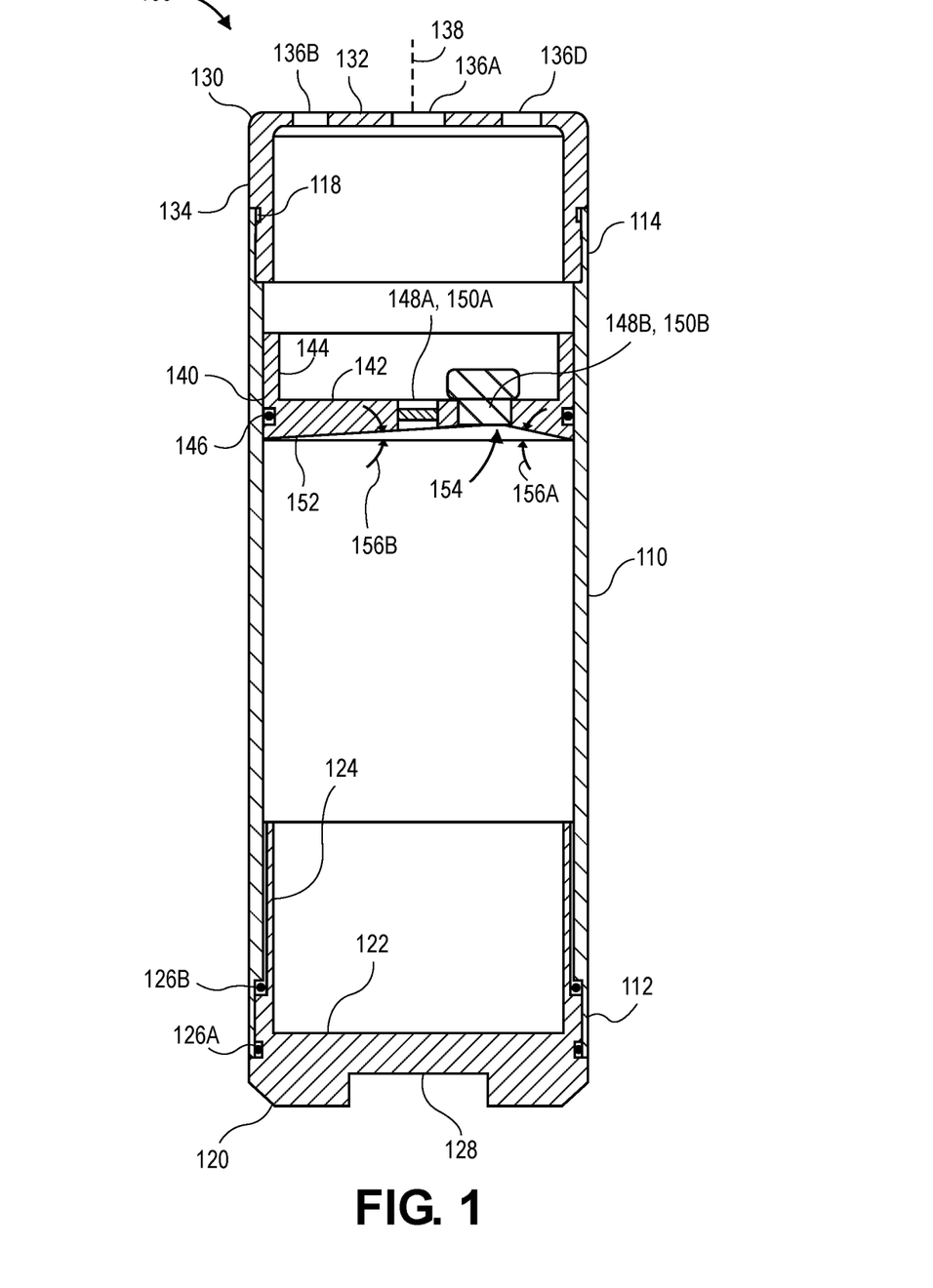
FIG. 1 illustrates a cross-sectional side view of a device for storing a fluid, according to an embodiment.
Figure 2:
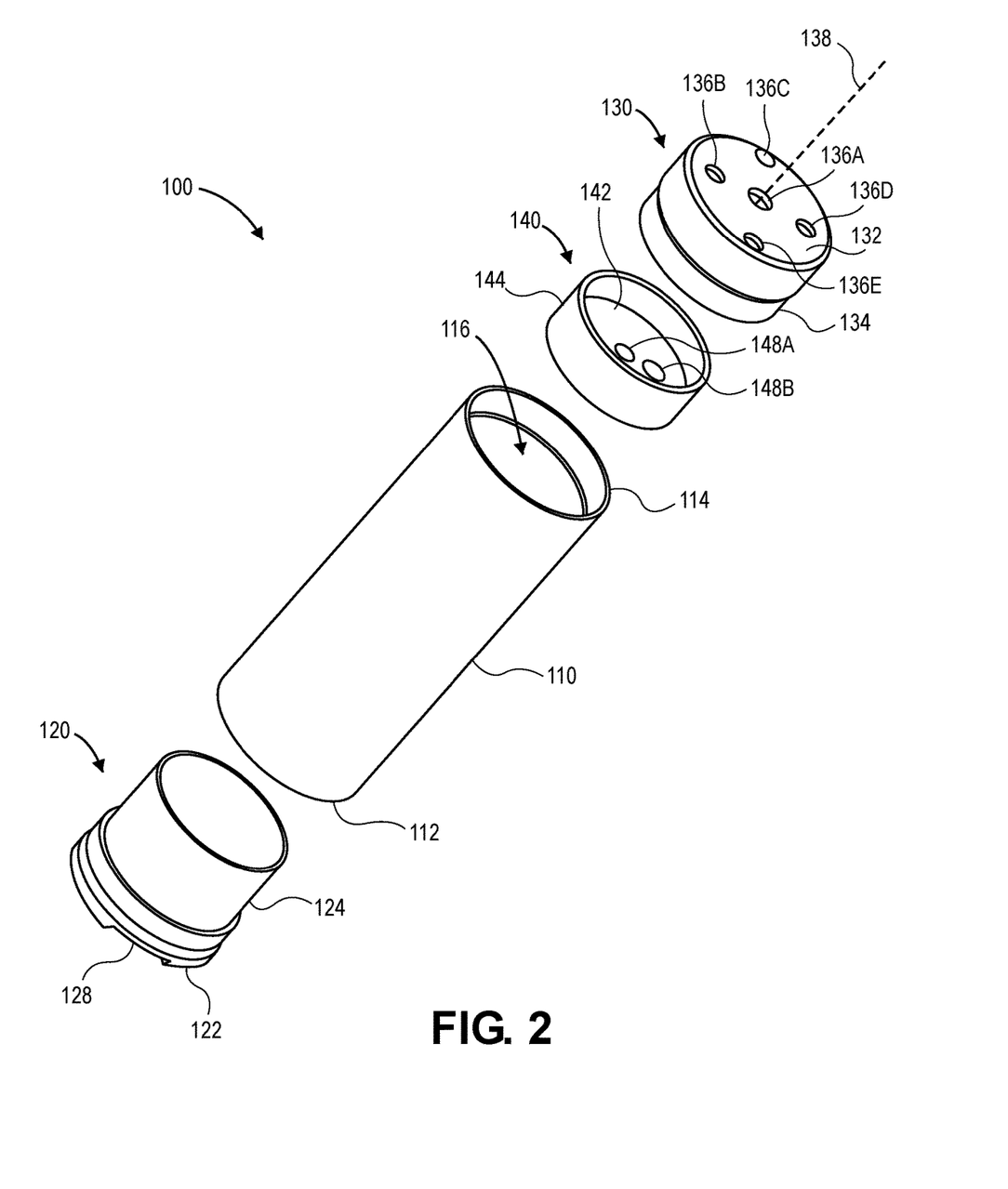
FIG. 2 illustrates an exploded perspective view of the device, according to an embodiment.

FIG. 1 illustrates a cross-sectional side view of a device 100 for storing a fluid, and FIG. 2 illustrates an exploded perspective view of the device 100, according to an embodiment. The fluid may be or include a drilling fluid (also referred to as a drilling mud). In one embodiment, the fluid may be collected from a wellbore. In another embodiment, the fluid may be prepared/mixed by a person (e.g., in a lab).

The device 100 may include a housing 110. As shown, the housing 110 may be substantially cylindrical; however, other shapes are also possible. A wall of the housing 110 may have a thickness from about 0.5 mm to about 5 mm or about 1 mm to about 3 mm. The housing 110 may be made from a metal, a polymer, a ceramic material, or a combination thereof. The housing 110 may have a first (e.g., lower) end 112 and a second (e.g., upper) end 114. The housing 110 may also have a bore 116 formed axially therethrough (see FIG. 2). The bore 116 may also be referred to as an inner volume.

The device 100 may also include a first (e.g., lower) cap 120. The lower cap 120 may include a base 122 and a wall 124 that extends upwardly from the base 122 such that the lower cap 120 may serve or function as a "cup." Thus, the lower cap 120 may define an inner volume. As shown, in FIG. 1, when the device 100 is assembled, the inner volumes of the housing 110 and the lower cap 120 may at least partially overlap.

The lower cap 120 may be configured to be coupled to the lower end 112 of the housing 110. More particularly, the wall 124 may be inserted at least partially into the lower end 112 of the housing 110. The lower cap 120 may have threads on an outer surface thereof that are configured to engage corresponding threads on the inner surface of the lower end 112 of the housing 110.

One or more seals (two are shown: 126A, 126B) may be positioned at least partially between the housing 110 and the lower cap 120 to form a fluid-tight seal between the housing 110 and the lower cap 120. A first (e.g., lower) seal 126A may be positioned radially between the housing 110 and the lower cap 120. A second (e.g., upper) seal 126B may be positioned radially and/or axially between the housing 110 and the lower cap 120. In another embodiment, the first seal 126A, the second seal 126B, or another seal may be located radially between the housing 110 and the lower cap 120, proximate to the upper end of the wall 124.

A lower outer surface of the base 122 may define a slot 128 that is configured to facilitate insertion into and/or engagement with a vessel (e.g., a consistometer), as discussed below.

The device 100 may also include a second (e.g., upper) cap 130. The upper cap 130 may include a base 132 and a wall 134 that extends downwardly from the base 132. The upper cap 130 may be configured to be coupled to (or integral with) the upper end 114 of the housing 110. More particularly, the wall 134 may be inserted at least partially into the upper end 114 of the housing 110. The upper cap 130 may have threads on an outer surface thereof that are configured to engage corresponding threads on the inner surface of the upper end 114 of the housing 110. In one embodiment, the wall 134 of the upper cap 130 may also include an annular recess 118 formed in the outer (e.g., radial) surface thereof. The threads of the upper cap 130 may be positioned below the annular recess 118, and the annular recess 118 may serve as thread relief for the upper cap 130. Although not shown, in another embodiment, the upper end 114 of the housing 110 may include a protrusion that extends (e.g., radially) inward that may be received (e.g., snapped) into the annular recess 118 to secure the upper cap 130 onto the housing 110. In this particular embodiment, the threads may be omitted.

The upper cap 130 may have one or more holes (five are shown: 136A-136E) formed therethrough. The holes 136A-136E may extend from an upper/outer surface of the base 132 to a lower/inner surface of the base 132 so as to provide communication therethrough to the inner volume of the housing 110. The first hole 136A may be in a center portion of the base 132. For example, the first hole 136A may be aligned with a central longitudinal axis 138 through the housing 110, the upper cap 130, or both. The holes 136B-136E may be positioned radially outward from the axis 138. The holes 136B-136E may be circumferentially offset from one another (e.g., by 90°).

One or more of the holes 136A-136E may be configured to receive (i.e., provide purchase for) any tool that is used to retrieve the device 100 from a vessel (e.g., a consistometer), as discussed below. In addition, one or more of the holes 136A-136E may be configured to have a thermowell and/or temperature sensor positioned at least partially therein to aid in temperature control of the device 100. In one embodiment, a thermo-sensor may be positioned at least partially within the upper cap 130 (e.g., in the hole 136A). One or more of the holes (e.g., holes 136B-136E) may provide access to insert and/or remove the plug 150B (described below) with the upper cap 130 coupled to the housing 110.

The device 100 may also include a piston 140 that is configured to be positioned at least partially within the housing 110. The piston 140 may include a base 142 and a wall 144 that extends from the base 142. As shown, the wall 144 extends upwardly from the base 142. In other embodiments, the wall 144 may also or instead extend downwardly from the base 142. One or more seals (one is shown: 146) may be positioned at least partially between the housing 110 and the piston 140 to form a fluid-tight seal between the housing 110 and the piston 140.

The piston 140 may have one or more holes (two are shown: 148A, 148B) formed therethrough. The holes 148A, 148B may extend from an upper surface of the base 142 to a lower surface of the base 142. The first hole 148A may be in a center portion of the base 142. For example, the first hole 148A may be aligned with the axis 138. The second hole 148B may be positioned radially outward from the axis 138.

The piston 140 may also include a rupture disk 150A (see FIG. 1) that is positioned at least partially within the first hole 148A. The rupture disk 150A is configured to prevent fluid from flowing through the first hole 148A. However, the rupture disk 150A may be configured to rupture in response to a pressure differential across the piston 140 (and the rupture disk 150A) exceeding a predetermined threshold. The rupture disk 150A may help to maintain the integrity of the device 100 (e.g., prevent the device 100 from bursting or collapsing) in the case of a process upset. For example, if the piston 140 becomes stuck and cannot balance the pressure between the drilling fluid and the hydraulic fluid, the rupture disk 150A may rupture to preserve the device 100. The rupture disk 150A may also or instead rupture if the device 100 is overfilled, which may cause thermal expansion pinning the piston 140 to the upper cap 130.

The piston 140 may also include a plug (also referred to as a "bleed plug") 150B (see FIG. 1) that is positioned at least partially within the second hole 148B. The plug 150B is configured to prevent fluid from flowing through the second hole 148B. The plug 150B may have threads on an outer surface thereof that are configured to engage with threads on an inner surface of the base 142 that defines the second hole 148B. The second hole 148B and/or the plug 150B may be radially offset from the axis 138, which may help prevent the piston 140 from turning/rotating when the plug 150B is being turned/rotated to tighten and/or loosen the plug 150B.

The lower surface 152 of the piston 140 (e.g., the base 142) may be at least partially concave. For example, the lower surface 152 may be substantially conical or frusto-conical and define a pocket 154. The pocket 154 may slope upward toward the second hole 148B and/or the plug 150B. Due to the second hole 148B and/or the plug 150B being radially outward from the axis 138, an angle between the lower surface 152 that defines the pocket 154 and the axis 138 may vary proceeding around the axis 138. For example, the angle 156A may be greater than the angle 156B. As described in greater below, the pocket 154 may help to direct air through the second hole 148B when the piston 140 is pressed downward into the fluid.

Figure 3A:
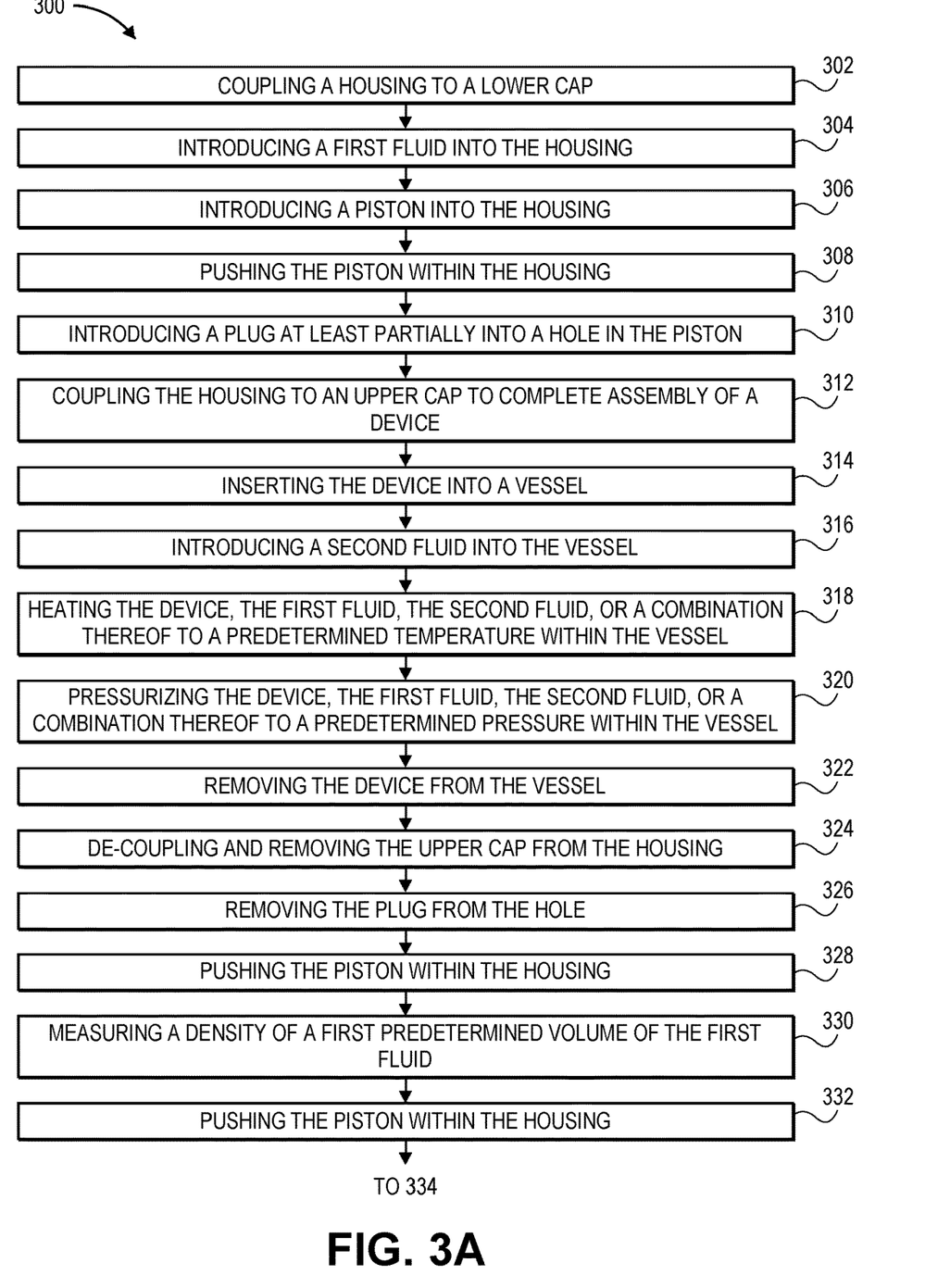
FIGS. 3A and 3B illustrate a flowchart of a method for performing a sag measurement on the fluid, according to an embodiment.
Figure 3B:
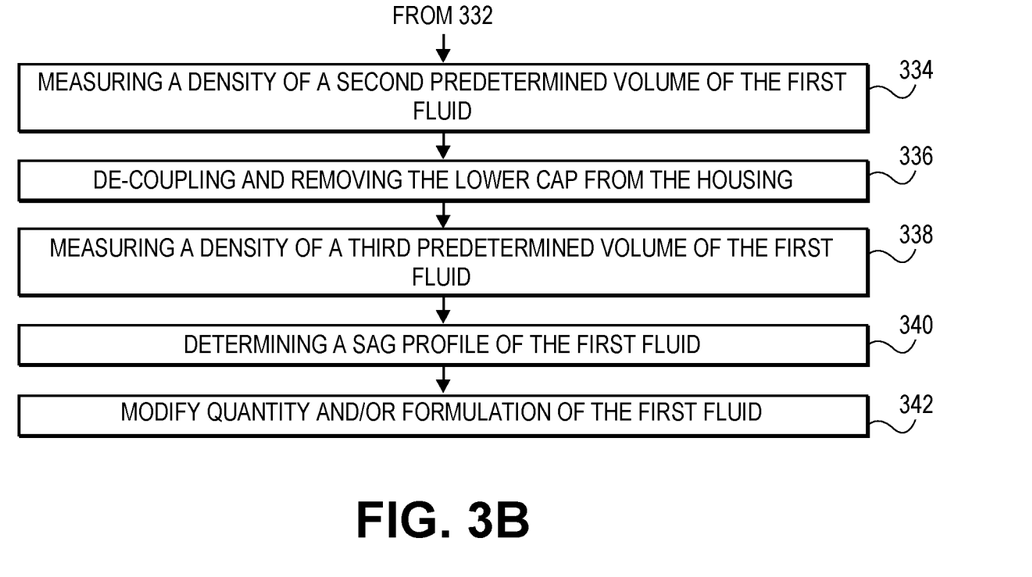

FIGS. 3A and 3B illustrate a flowchart of a method 300 for performing a sag measurement on the fluid, according to an embodiment. More particularly, the method 300 may determine a sag characterization of a fluid under increased (e.g., ultrahigh) temperature and pressure conditions. An illustrative order of the method 300 is provided below; however, one or more portions of the method 300 may be performed in a different order, performed simultaneously, repeated, or omitted. FIGS. 4-12 illustrate various steps of the method 300.

Figure 4:
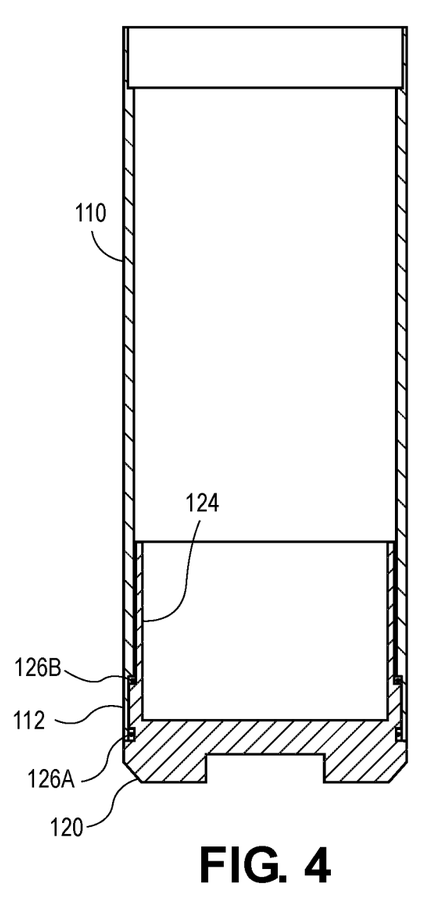
FIG. 4 illustrates a cross-sectional side view of a housing and a lower cap of the device, according to an embodiment.

The method 300 may include coupling the housing 110 to the lower cap 120, as at 302. This is shown in FIG. 4. Coupling the housing 110 to the lower cap 120 may include inserting the wall 124 of the lower cap 120 at least partially into the lower end 112 of the housing 110, and threading the housing 110 and the lower cap 120 together. The seals 126A, 126B may be positioned at least partially between the housing 110 and the lower cap 120.

Figure 5:
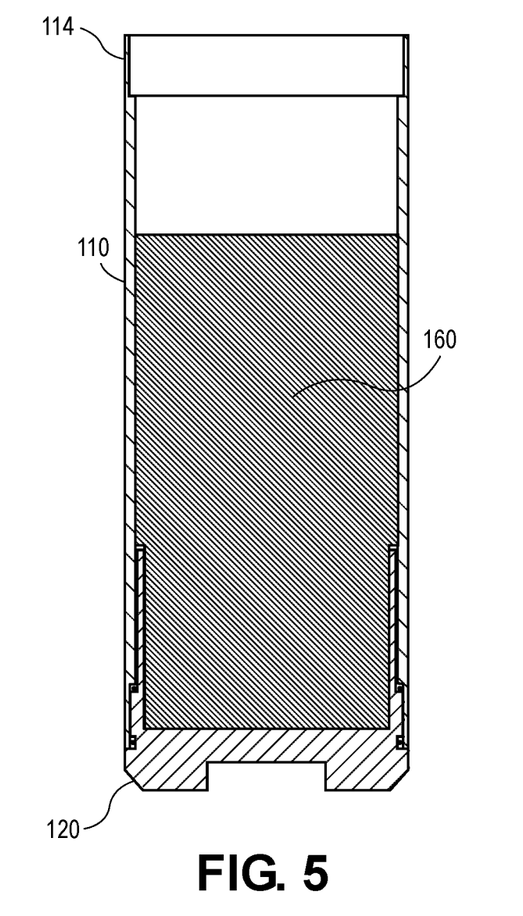
FIG. 5 illustrates a cross-sectional side view of the housing and the lower cap with a fluid therein, according to an embodiment.

The method 300 may also include introducing a first fluid 160 into the housing 110, as at 304. This is shown in FIG. 5. Introducing the first fluid 160 into the housing 110 may include pouring the first fluid 160 into the upper end 114 of the housing 110. The first fluid 160 may be positioned within the inner volume of the housing 110, the lower cap 120, or a combination thereof. The first fluid 160 may fill from about 50% to about 90% or about 60% to about 80% of the inner volume(s). The first fluid 160 may be or include the drilling fluid (e.g., drilling mud).

Figure 6:
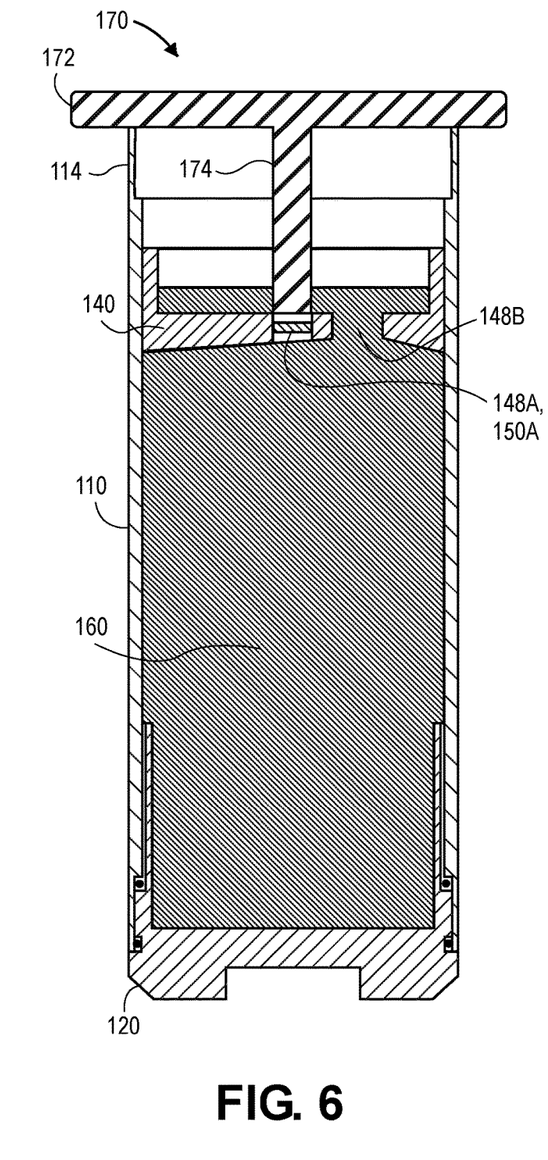
FIG. 6 illustrates a cross-sectional side view of a first actuator pushing downward on a piston in the housing, according to an embodiment.

The method 300 may also include introducing the piston 140 into the housing 110, as at 306. This is shown in FIG. 6. The piston 140 may be introduced through the upper end 114 of the housing 110. The piston 140 may be positioned at least partially above the first fluid 160. In at least one embodiment, the rupture disk 150A may be positioned at least partially within the hole 148A when the piston 140 is introduced into the housing 110.

The method 300 may also include pushing the piston 140 within the housing 110, as at 308. This is also shown in FIG. 6. The piston 140 may be pushed downward toward the lower cap 120 using a first actuator 170 until a portion of the first fluid 160 flows upward through the hole 148B. The pocket 154 in the lower surface 152 of the piston 140 may funnel the air through the hole 148B as the piston 140 moves downward.

Once the first fluid 160 flows through the hole 148B, the user may conclude that there is no gas (e.g., air) left in the housing 110 below the piston 140, which may be beneficial for the following reasons. If air is trapped under the piston 140, the air may be dissolved into the first fluid 160 due to the pressure, temperature, and time in the vessel, as discussed below. When the device 100 is depressurized, the air may break-out and migrate in the device 100, which may disturb the upper layer of the first fluid 160 in the device 100. Any air trapped under the piston 140 may also or instead effervesce the first fluid 160 when the plug 150B is removed. In addition, any air trapped under the piston 140 may compress to near-zero volume, which may move the initial position of the piston 140 relative to the volumes of the samples taken.

In addition, the position of the piston 140 may help to provide testing consistency. More particularly, the sample volumes of the first fluid 160 may be substantially consistent to ovation comparative sag data. If different volumes of the first fluid are tested multiple times, the results may be different. In addition, the initial fill volume of the first fluid 160 in the housing 110 may help to ensure pressure and temperature induced density changes can be accommodated by the movement range of the piston 140.

Figure 7:
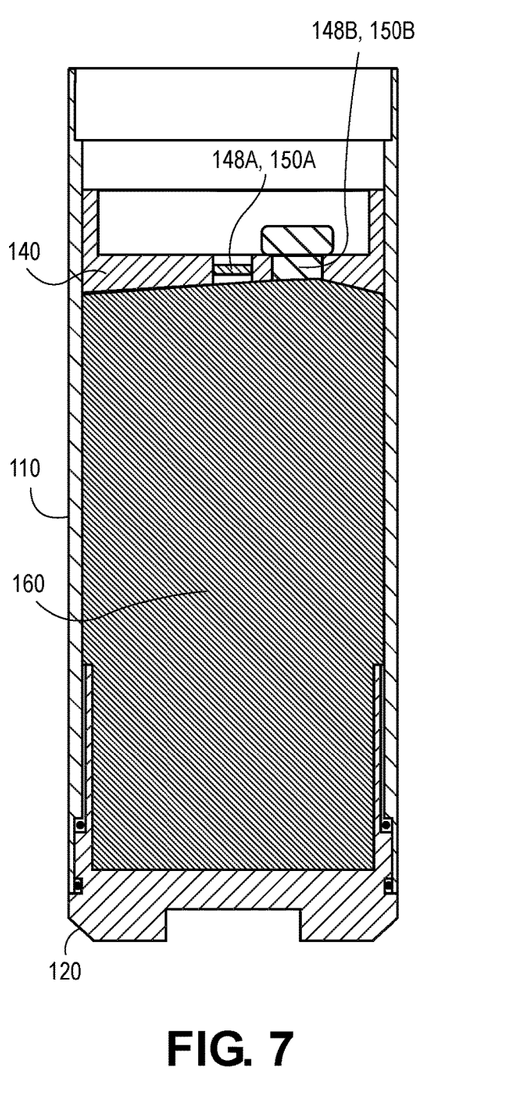
FIG. 7 illustrates a cross-sectional side view of a plug introduced into a hole in the piston, according to an embodiment.

The first actuator 170 may be or include a T-handle with a shaft 172 and a handle 174. The portion of the first fluid 160 that flows through the hole 148B may be less than about 5%, less than about 3%, or less than about 1% of the first fluid 160 in the housing 110. The first fluid 160 that flows through the hole 148B may then be cleaned (e.g., vacuumed). This is shown in FIG. 7.

The method 300 may also include introducing the plug 150B at least partially into the hole 148B, as at 310. This is also shown in FIG. 7. Introducing the plug 150B at least partially into the hole 148B may include screwing the plug 150B into place within the piston 140 so that the plug 150B prevents the first fluid 160 from flowing through the hole 148B.

Figure 8:
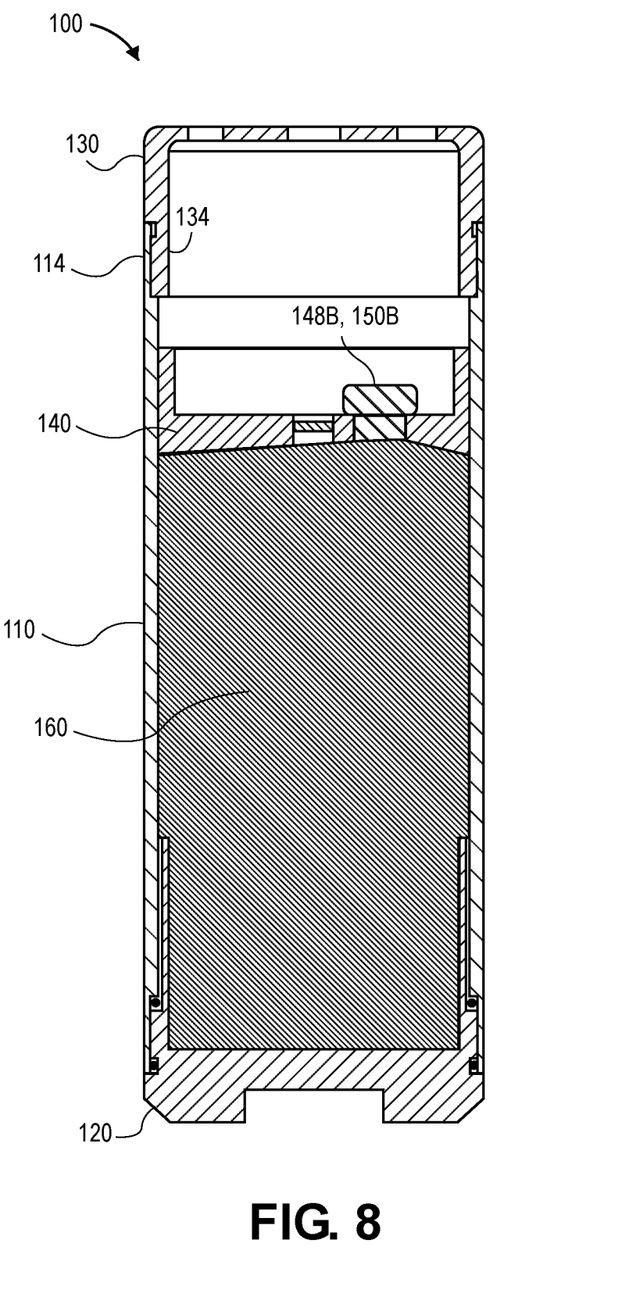
FIG. 8 illustrates a cross-sectional side view of an upper cap coupled to the housing, according to an embodiment.

The method 300 may also include coupling the housing 110 to the upper cap 130, as at 312. This is shown in FIG. 8. Coupling the housing 110 to the upper cap 130 may include inserting the wall 134 of the upper cap 130 at least partially into the upper end 114 of the housing 110, and threading the housing 110 and the upper cap 130 together. This may complete the assembly of the device 100.

Figure 9:
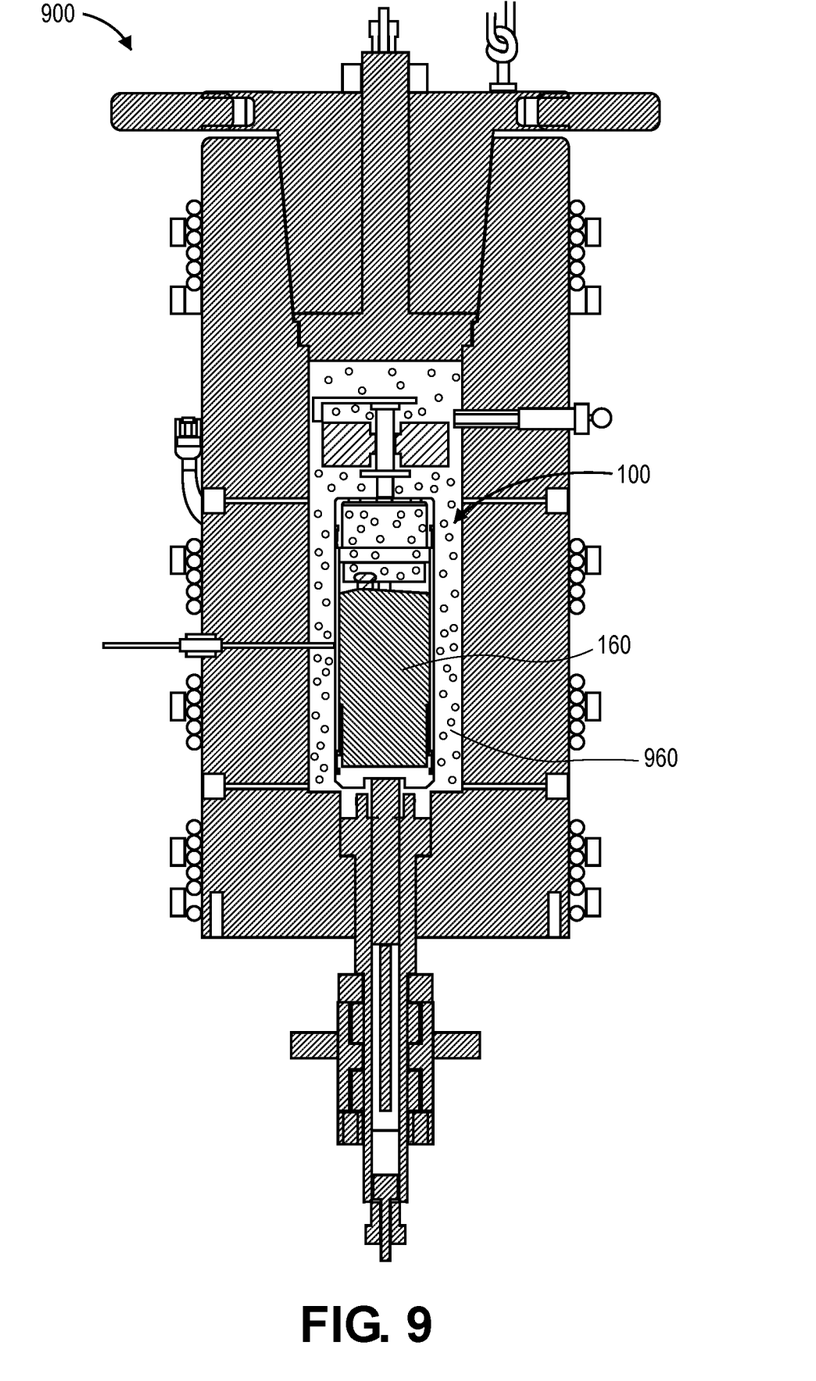
FIG. 9 illustrates a cross-sectional side view of the device positioned within a vessel, according to an embodiment.

The method 300 may also include inserting the device 100 into a vessel 900, as at 314. This is shown in FIG. 9. The device 100 may prevent the first fluid 160 from contacting and/or contaminating the inside of the vessel 900. This may speed up the cleaning of the vessel 900 as well as prevent corrosion inside the vessel 900, which may be caused by the first fluid 160. In one embodiment, the vessel 900 may be or include a pressure vessel, such as a consistometer. However, in other embodiments, the vessel 900 may be or include any vessel that is configured to perform the one or more portions high temperature high pressure (HTHP) testing described below.

The method 300 may also include introducing a second fluid 960 into the vessel 900, as at 316. This is also shown in FIG. 9. The second fluid 960 may be or include a hydraulic fluid 960. The second fluid 960 may at least partially surround the device 100. In other words, the device 100 may be suspended or submerged within the second fluid 960. The second fluid 960 may flow at least partially into the device 100 through the holes 136A-136E in the upper cap 130 (see FIGS. 1 and 2). The piston 140 may provide a barrier between the first fluid 160 and the hydraulic fluid 960, which prevents the fluids 160, 960 from mixing. This may prevent the second fluid 960 from contaminating the first fluid 160, which may invalidate the test. The piston 140 may move axially within the housing 110 in response to a pressure differential between the first fluid 160 and the second fluid 960. The second fluid 960 may be or include water, oil, glycols, or a combination thereof.

The method 300 may also include heating the device 100, the first fluid 160, the second fluid 960, or a combination thereof to a predetermined temperature within the vessel 900, as at 318. The predetermined temperature may be from about 150° C. to about 315° C. (600° F.) or about 175° C. to about 250° C.

The method 300 may also include pressurizing the device 100, the first fluid 160, the second fluid 960, or a combination thereof to a predetermined pressure within the vessel 900, as at 320. The predetermined pressure may be from about 130 MPa to about 450 MPa or about 200 MPa to about 275 MPa (40,000 PSI).

The temperature and pressure may be coordinated (e.g., increased and/or decreased simultaneously). If the temperature is increased, the pressure will increase. The pressure may increase fluid viscosity hindering barite sag while the temperature thins the fluid promoting sag. The pressure is increased to the levels discussed above to realistically model the downhole environment. Conventional low-pressure, high temperature tests indicate more sag than actually occurs under higher pressure field conditions. In one embodiment, the first fluid 160 may not be agitated within the device 100. Thus, if the first fluid 160 sags, there may be no recovery. The device 100 may remain within the vessel 900 at the high temperature and high pressure (HTHP) for a predetermined amount of time. The predetermined amount of time may be one or more days, weeks, or months.

Maintaining the first fluid 160 at the HTHP for the predetermined duration may be referred to as "aging the fluid." Aging the fluid may simulate downhole conditions (e.g., temperature and pressure in a wellbore). Fluids under these conditions may exhibit density stratification due to weight material settlement (i.e., sag) and/or base fluid syneresis. In the case of sag, a vertical density gradient occurs, as the weighting material may settle, resulting in higher fluid densities in the lower portion of the housing 110 and/or the lower cap 120. In the case of emulsions, "free-oil" may rise to the top of the sample in the upper portion of the housing 110. The measurements discussed below may determine the amount of sag and/or free-oil resulting from "aging" a representative sample of drilling fluids under elevated temperature and pressure conditions.

The method 300 may also include removing the device 100 from the vessel 900, as at 322. As mentioned above, the temperature and pressure within the vessel 900 may be coordinated. For example, the temperature and pressure of the device 100 and the first fluid 160 may be decreased simultaneously. The device 100 may be removed after the predetermined amount of time when the device 100 and/or the first fluid 160 are at the ambient temperature and pressure.

Figure 10:
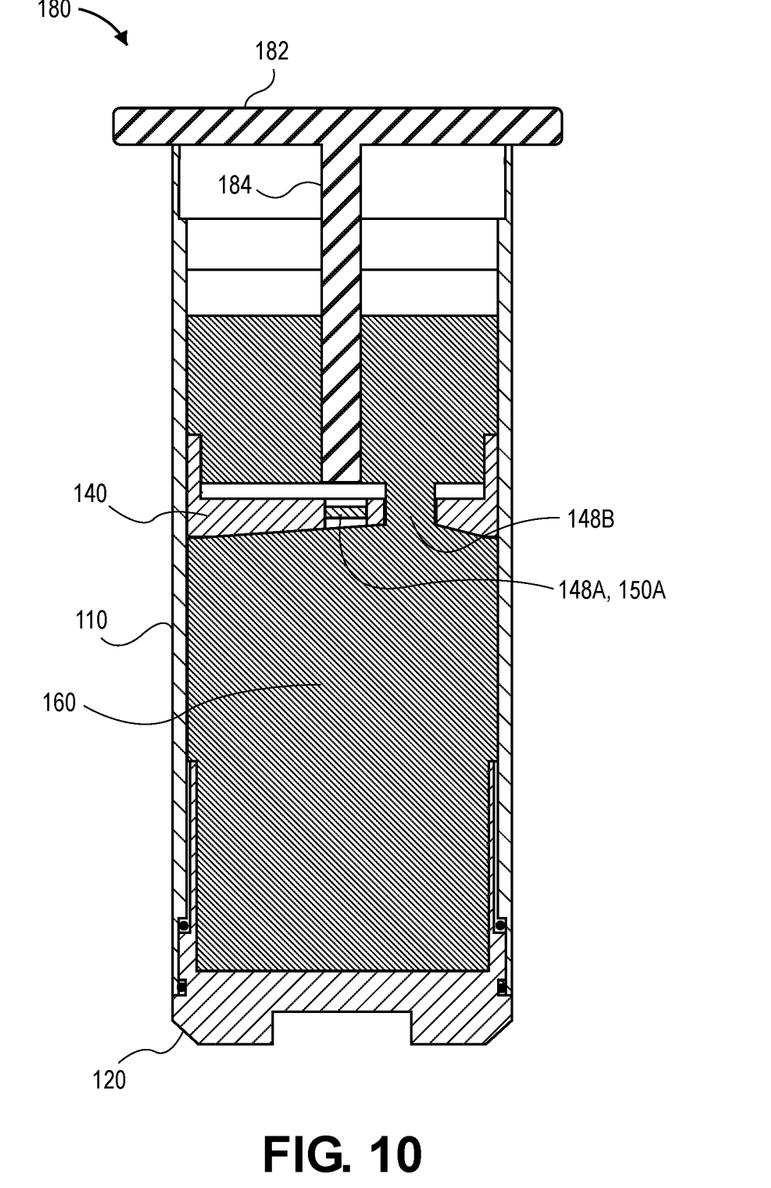
FIG. 10 illustrates a cross-sectional side view of a second actuator pushing downward on the piston in the housing, according to an embodiment.

The method 300 may also include de-coupling and removing the upper cap 130 from the housing 110, as at 324. This is shown in FIG. 10. The method 300 may also include removing the plug 150B from the hole 148B, as at 326. This is also shown in FIG. 10.

The method 300 may also include pushing the piston 140 within the housing 110, as at 328. This is also shown in FIG. 10. The piston 140 may be pushed downward within the housing 110 using a second actuator 180. The second actuator 180 may be or include a T-handle with a shaft 182 and a handle 184. The shaft 182 of the second actuator 180 may be longer than the shaft 172 of the first actuator 170. In another embodiment, the first and second actuators 170 may be the same actuator, and the actuator may be pushed farther down in step 328 than in step 308.

The piston 140 may be pushed downward toward the lower cap 120 using the second actuator 180 until the handle 184 of the second actuator 180 contacts the upper end 114 of the housing 110. This may cause a first predetermined volume of the first fluid 160 to flow upward through the hole 148B such that the first predetermined volume of the first fluid 160 is positioned above the piston 140. In one embodiment, the first predetermined volume may be from about 20% to about 50% or about 25% to about 40% (e.g., one third) of the volume of the first fluid 160 in the housing 110.

The method 300 may also include measuring a density of the first predetermined volume of the first fluid 160, as at 330. The first predetermined volume of the first fluid 160 may be removed from the housing 110 prior to the density being measured.

Figure 11:
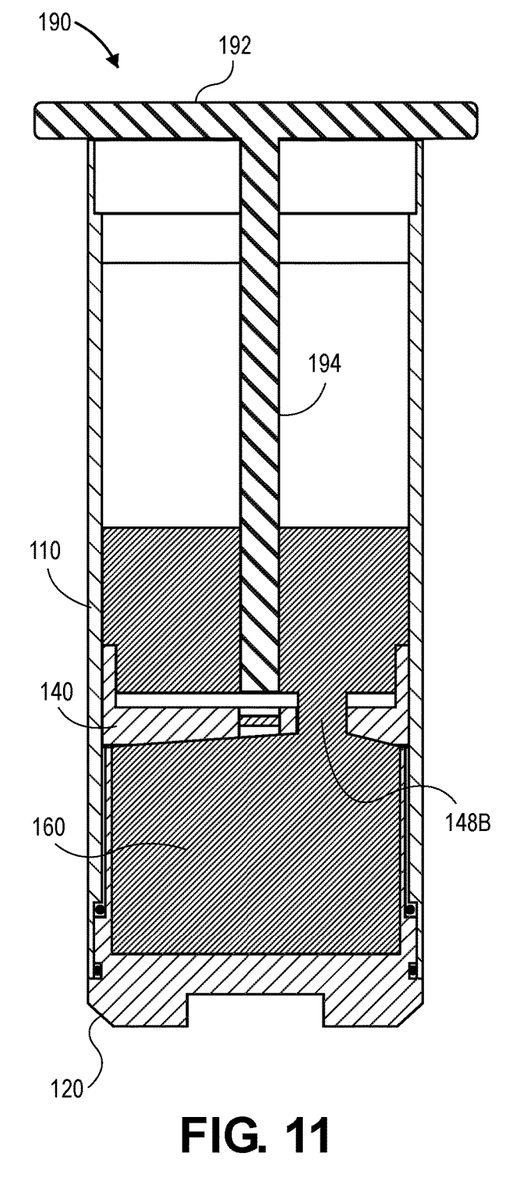
FIG. 11 illustrates a cross-sectional side view of a third actuator pushing downward on the piston in the housing, according to an embodiment.

The method 300 may also include pushing the piston 140 within the housing 110, as at 332. This is shown in FIG. 11. The piston 140 may be pushed within the housing 110 using a third actuator 190. The third actuator 190 may be or include a T-handle with a shaft 192 and a handle 194. The shaft 192 of the second actuator 190 may be longer than the shaft 172 of the first actuator 170 and/or the shaft 182 of the second actuator 180. In another embodiment, the third actuator 190 may be the same as the first actuator 170 and/or the second actuator 180, and the actuator may be pushed farther down in step 332 than in step 308 and/or 328.

The piston 140 may be pushed downward toward the lower cap 120 using the third actuator 190 until the handle 194 of the third actuator 190 contacts the upper end 114 of the housing 110. In another embodiment, the piston 140 may be pushed downward toward the lower cap 120 until the piston 140 contacts the upper end of the wall 124 of the lower cap 120, which may serve as a stop. This may cause a second predetermined volume of the first fluid 160 to flow upward through the hole 148B such that the second predetermined volume of the first fluid 160 is positioned above the piston 140. In one embodiment, the second predetermined volume may be from about 20% to about 50% or about 25% to about 40% (e.g., one third) of the volume of the first fluid 160 in the housing 110.

The method 300 may also include measuring a density of the second predetermined volume of the first fluid 160, as at 334. The second predetermined volume of the first fluid 160 may be removed from the housing 110 prior to the density being measured.

After the second predetermined volume of the fluid is removed from the housing 110, a third predetermined volume of the first fluid 160 may remain within the housing 110 (e.g., in the lower cap 120). In one embodiment, the third predetermined volume may be from about 20% to about 50% or about 25% to about 40% (e.g., one third) of the volume of the first fluid 160 in the housing 110.

Figure 12:
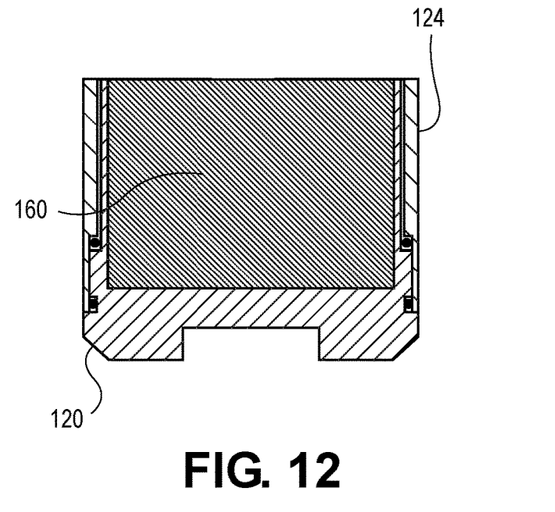
FIG. 12 illustrates a cross-sectional side view of the lower cap with the fluid therein, according to an embodiment.

The method 300 may also include de-coupling and removing the lower cap 120 from the housing 110, as at 336. This is shown in FIG. 12. The third predetermined volume of the first fluid 160 may be/remain within the lower cap 120, which may serve as a "cup."

The method 300 may also include measuring a density of the third predetermined volume of the first fluid 160, as at 338. The third predetermined volume of the first fluid 160 may be removed from the housing 110 and/or the lower cap 120 prior to the density being measured.

The method 300 may also include determining a sag profile of the first fluid 160, as at 340. In one embodiment, the sag profile may be determined based at least partially upon the density of the first predetermined volume, the second predetermined volume, the third predetermined volume, or a combination thereof. In another embodiment, the sag profile may also or instead be determined using non-destructive techniques such as X-ray, nuclear magnetic resonance (NMR), ultrasonic, etc. after aging the fluid. More particularly, the housing 110 may have thin walls (e.g., with a thickness that is less than about 2 mm, less than about 1 mm, or less than about 0.5 mm), and the housing 110 may be made of a material that is substantially transparent to the measurement technique. For example, the device 100 (e.g., the housing 110) may be made of a nonmagnetic material when the measurement technique is NMR. The density may be measured as a function of height by translating one or more sensors up and down the device 100 (e.g., the housing 110). The sensor(s) may also or instead be used to measure the local density proximate to the top (e.g., through the base 142 of the piston 140) and proximate to the bottom (e.g., through the lower cap 120), which may be used to determine the sag profile. In an embodiment, these non-destructive techniques may augment the manual density gradient determination (e.g., which is based on the density of the first predetermined volume, the second predetermined volume, the third predetermined volume, or a combination thereof).

If the sag profile is outside of a predetermined threshold, the method 300 may also include modifying a quantity or formulation of the first fluid 160, as at 342. Once the quantity and/or formulation of the first fluid 160 has been modified, the method 300 may loop back to 304 to test the new quantity/formulation.

The method 300 may be used to verify the first fluid's ability to maintain a homogenous density after being subjected to downhole conditions for a set time period. The performance of the first fluid is determined by a characterizing vertical density gradient after aging. The method 300 accomplishes this by collecting volumes of the first fluid above the piston, which is pushed preset distances into the sample, and measuring the respective densities of those volumes to determine the vertical density gradient. In some cases, the "free-oil" is removed from the top of the sample, and then the density gradient is determined. In other cases, the free-oil is not removed, and the density gradient is determined. The test is performed to determine the degree to which the density varies throughout the volume(s) in the device, and whether this deviation is acceptable (e.g., based on a customer's specification).

As used herein, the terms "inner" and "outer"; "up" and "down"; "upper" and "lower"; "upward" and "downward"; "upstream" and "downstream"; "above" and "below"; "inward" and "outward"; and other like terms as used herein refer to relative positions to one another and are not intended to denote a particular direction or spatial orientation. The terms "couple," "coupled," "connect," "connection," "connected," "in connection with," and "connecting" refer to "in direct connection with" or "in connection with via one or more intermediate elements or members."

The foregoing description, for purposes of explanation, used specific nomenclature to provide a thorough understanding of the disclosure. However, it will be apparent to one skilled in the art that the specific details are not required in order to practice the systems and methods described herein. The foregoing descriptions of specific examples are presented for purposes of illustration and description. They are not intended to be exhaustive of or to limit this disclosure to the precise forms described. Many modifications and variations are possible in view of the above teachings. The examples are shown and described in order to best explain the principles of this disclosure and practical applications, to thereby enable others skilled in the art to best utilize this disclosure and various examples with various modifications as are suited to the particular use contemplated. It is intended that the scope of this disclosure be defined by the claims and their equivalents below.

What is claimed is:

1. A device for aging a drilling fluid, the device comprising:
    a housing;
    a lower cap that is configured to be coupled to or integral with a lower end of the housing;
    an upper cap that is configured to be coupled to an upper end of the housing, wherein the upper cap has an upper cap hole formed therethrough; and
    a piston that is configured to be positioned within the housing and between the lower and upper caps, wherein the piston is configured to move axially within the housing in response to a pressure differential across the piston, and wherein the piston has a first piston hole formed therethrough;
    wherein the piston has a second piston hole formed therethrough, and
wherein the device further comprises a rupture disk positioned at least partially within the second piston hole;
    wherein the second piston hole is substantially aligned with a central longitudinal axis through the piston, and wherein the first piston hole is radially outward from the central longitudinal axis.

2. The device of claim 1, wherein the lower cap comprises a base and a wall extending upwardly from the base, wherein the wall is configured to be positioned at least partially within the housing such that an inner volume of the lower cap at least partially overlaps with an inner volume of the housing, and wherein the wall comprises threads on an outer surface thereof that are configured to engage with corresponding threads on an inner surface of the housing to couple the lower cap to the housing.

3. The device of claim 1, further comprising a first seal positioned radially between the housing and the lower cap.

4. The device of claim 3, further comprising a second seal positioned radially and axially between the housing and the lower cap.

5. The device of claim 1, further comprising a plug that is configured to be positioned at least partially within the first piston hole to prevent fluid from flowing through the first piston hole.

6. The device of claim 5, wherein the plug comprises threads on an outer surface thereof that are configured to engage with corresponding threads on an inner surface of the piston that defines the first piston hole.

7. The device of claim 1, wherein a lower surface of the piston is concave and slopes upward toward the second piston hole.

8. The device of claim 7, wherein an angle between the lower surface and a central longitudinal axis through the piston varies proceeding around the central longitudinal axis.

9. A system for determining a sag profile of a drilling fluid that has been exposed to elevated temperature and pressure conditions, the system comprising:
a device comprising:
a housing that is substantially cylindrical and defines an inner volume, wherein the inner volume is configured to receive the drilling fluid;
a lower cap that is coupled to a lower end of the housing, wherein the lower cap comprises a base and a wall extending upwardly from the base, wherein the wall is configured to be positioned at least partially within the housing such that an inner volume of the lower cap at least partially overlaps with the inner volume of the housing, and wherein the wall comprises threads on an outer surface thereof that are configured to engage with corresponding threads on an inner surface of the housing;
an upper cap coupled to an upper end of the housing, wherein the upper cap has an upper cap hole formed therethrough to allow a hydraulic fluid to flow therethrough into the inner volume of the housing;
a piston positioned within the housing and between the lower and upper caps, wherein the piston is configured to move axially within the housing in response to a pressure differential between the drilling fluid and the hydraulic fluid across the piston, and wherein the piston has a first piston hole and a second piston hole formed therethrough,
a plug configured to be positioned at least partially within the first piston hole; and
a rupture disk configured to be positioned at least partially within the second piston hole; and
a vessel defining an inner volume, wherein the device is configured to be introduced into the inner volume of the vessel, and wherein a temperature and a pressure of the drilling fluid in the device are configured to be increased while the device is positioned within the vessel.

10. The system of claim 9, wherein the piston prevents the drilling fluid from mixing with the hydraulic fluid.

11. The system of claim 9, wherein the second piston hole is substantially aligned with a central longitudinal axis through the piston, and wherein the first piston hole is radially outward from the central longitudinal axis.

12. The system of claim 9 wherein a lower surface of the piston is concave and slopes upward toward the second piston hole.

13. The system of claim 9, wherein an angle between a lower surface of the piston and a central longitudinal axis through the piston varies proceeding around the central longitudinal axis.

14. A method for determining a sag profile of a first fluid that has been exposed to elevated temperature and pressure conditions, the method comprising:
introducing the first fluid into a housing of a device;
introducing a piston into the housing, wherein the piston is at least partially above the first fluid;
coupling an upper cap to an upper end of the housing;
inserting the device into a vessel;
heating the first fluid to a predetermined temperature within the vessel; and
pressurizing the first fluid to a predetermined pressure within the vessel further comprising:
removing the device from the vessel;
de-coupling the upper cap from the upper end of the housing;
removing a plug from a first piston hole in the piston;
pushing the piston downward within the housing until a first predetermined volume of the first fluid flows through the first piston hole;
measuring a density of the first predetermined volume of the first fluid; and
determining the sag profile of the first fluid based at least partially upon the density of the first predetermined volume of the first fluid.

15. The method of claim 14, further comprising:
pushing the piston downward within the housing until at least a portion of the first fluid flows upward through a first piston hole in the piston; and
introducing a plug into the first piston hole after the at least a portion of the first fluid flows upward through the first piston hole.

16. The method of claim 14, further comprising introducing a second fluid into the vessel, wherein the second fluid flows into the housing through an upper cap hole in the upper cap, such that the second fluid is positioned between the piston and the upper cap, and wherein the piston prevents the first and second fluids from mixing.

17. The method of claim 14, further comprising:
pushing the piston downward within the housing until a second predetermined volume of the first fluid flows through the first piston hole;
measuring a density of the second predetermined volume of the first fluid;
de-coupling a lower cap from a lower end of the housing, wherein a third predetermined volume of the first fluid is within the lower cap;
measuring a density of the third predetermined volume of the first fluid; and
determining the sag profile of the first fluid based at least partially upon the density of the second predetermined volume of the first fluid and the third predetermined volume of the first fluid.

* * * * *